(12) United States Patent
Clark, Jr. et al.

(10) Patent No.: US 6,198,529 B1
(45) Date of Patent: Mar. 6, 2001

(54) AUTOMATED INSPECTION SYSTEM FOR METALLIC SURFACES

(75) Inventors: John C. Clark, Jr., Vestal; Earle W. Gillis; Christopher J. Majka, both of Apalachin; Matthew F. Seward, Windsor; Michael M. Westgate, Webster, all of NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/303,187

(22) Filed: Apr. 30, 1999

(51) Int. Cl.[7] ................................................. G01N 21/00
(52) U.S. Cl. ...................... 356/237.5; 356/394; 356/398
(58) Field of Search .................................. 356/237, 376, 356/394, 398

(56) References Cited

U.S. PATENT DOCUMENTS

| | | |
|---|---|---|
| 4,449,818 | 5/1984 | Yamaguchi et al. . |
| 4,675,730 | 6/1987 | Adomaitis et al. . |
| 5,030,008 | 7/1991 | Scott et al. . |
| 5,153,668 | 10/1992 | Katzir et al. . |
| 5,298,989 | 3/1994 | Tsukahara et al. . |
| 5,420,689 | 5/1995 | Siu . |
| 5,424,838 | 6/1995 | Siu . |
| 5,535,006 | 7/1996 | Telschow et al. . |
| 5,617,209 | 4/1997 | Svetkoff et al. . |

*Primary Examiner*—Frank G. Font
*Assistant Examiner*—Reginald A. Ratliff
(74) *Attorney, Agent, or Firm*—McGuire Woods, LLP; John R. Pivnichny

(57) ABSTRACT

An automated inspection system particularly adapted for detection and discrimination of surface irregularities of specularly reflecting and other materials, such as are employed in laminate chip carriers and printed circuit boards, includes an area scan image sensor allowing illumination sources to surround an area of a surface being inspected. The illumination source preferably provides either or both bright field and dark field illumination of the surface; developing generally complementary images of surface irregularities. A self-registering rules-driven process for developing inspection masks reduces alignment operations and improves performance. Image enhancement and morphological operations to detect surface irregularities are performed by digital signal processing, preferably using a dedicated vision processor. Masks screen potential defects to critical mounting and bonding surfaces accurately without requiring alignment of data or reference images to acquired images. Since potential defects are copied from acquired images and stored, verification of defects may be performed without further access to the inspected part and without removal of the part to another specialized apparatus, simplifying processing and increasing throughput and operator efficiency.

20 Claims, 12 Drawing Sheets

AUTOMATED INSPECTION SYSTEM FOR METALLIC SURFACES

BACKGROUND OF THE INVENTION

1. Field of the Invention

The present invention generally relates to automated optical inspection (AOI) systems and, more particularly, to automated inspection systems suitable for end-of-line semiconductor component manufacture and packaging, especially for inspection of metallic wirebond surfaces used with laminated chip carriers.

2. Description of the Prior Art

The art of semiconductor manufacturing has become sufficiently advanced that extremely complex devices can be fabricated at high integration density and very high manufacturing yield. Increases in chip integration density has required similar increases in chip carrier complexity and feature density to complement the advantages of reductions in connection length achieved on individual chips. In either case, the delicate metallurgical and chemical processes involved can be easily affected by contamination and other conditions which are not completely preventable and localized defects often occur. For this reason, sophisticated burn-in and testing arrangements and apparatus have been developed to assure full functionality and operational specifications of newly fabricated chips. Chip carriers, on the other hand, are subjected to inspection as well as functional testing prior to being populated with chips since many defect types which can occur in connections and pads cannot be detected by functional testing alone.

Inspection of chip carriers in various panel formats is commonly done prior to chip assembly to assure that reliable connections to the chips can be made by the package and support structure. In particular, for high reliability, wire bonding is currently preferred for making connections to chips although other techniques are known and in widespread use. Most of these techniques include the attachment of wires or leads to metallic connection pads and/or ring surfaces formed on the chip carrier. For a reliable connection to be made, connection pad or ring surfaces must be generally flat and free of contamination or voids (e.g. perforations in the pad) greater than a certain size. Variations from flatness (e.g. nodules and pits) and voids (e.g. holes extending through the metal layer) must be held within a closely controlled dimension to avoid compromise of the reliability of the connection or the reliability of the process by which the connection is made.

At the current state of the art, the wirebond surfaces are individually inspected by operators using low to medium power microscopes. Multiple inspections by different operators are considered to be required since inspection efficiency of individual operators is low. Further, the number of operators required for even modest production quantities engenders inconsistency in the inspection process. It can be readily understood that such an inspection process is labor-intensive and costly. The cost of such inspection thus adds significantly to the cost of the finished circuit packages while not insuring a maximal manufacturing yield.

Automated optical inspection (AOI) equipment that exists at the present time is intended for inspection of circuit traces on large panels. Imaging the traces and checking for the presence or absence of a trace or other feature is easily accomplished with these devices. With reflective white light inspection systems, some surface defects such as dishdowns (a substantial decrease in circuit trace height) may also be detected by such systems but these systems are not intended for more subtle surface imperfections and are inefficient and inaccurate when used for such a purpose. Further, the cameras used in these systems are line scan cameras providing only a single pass during scanning and thus are of limited flexibility relative to illumination of the object being inspected.

In this regard, the metallic surface of a wirebond pad is very difficult to illuminate in a consistent manner and may have variable surface textures due to minor process fluctuations which obscure certain types of defects to be detected. For example, acceptable surface roughness can create sufficient contrast under some lighting conditions that larger, unacceptable pits and nodules cannot be distinguished using simple segmentation thresholding methods.

Illumination cannot, as a practical matter, be altered consistent with the use of a line scan imaging device within an exposure in an automated inspection system. This prohibits inspection under multiple illumination conditions. Multiple imaging passes, in order to provide an alteration of illumination from exposure to exposure, is not considered a practical solution.

Further, AOI system generally image the entire surface of a part and transform either the test image or reference to align with the other for comparison through application of defect detection algorithms. The alignment process that must occur has drawbacks during the inspection process. First, it requires additional computation prior to the detection process which can become significant overhead for the system. Also, depending on the defect cetection methods used, slight pixel to pixel differences between test images and reference images of data that are otherwise unimportant can require detection sensitivity parameters to be lowered, thus lowering detectability for some types of defects.

Even with manual inspection by operators, identified potential defects must be verified, generally by another operator on another inspection machine. The transfer of a chip carrier having a suspected defect to another machine takes a significant amount of time, subjects the carrier to damage and inspection may be compromised by misalignment or misregistration in the further inspection machine. The change in operators is also a source of error.

In summary, inspection by operators is expensive and of low efficiency while existing automated optical inspection systems are ill-adapted to identify surface defects, particularly of metallic surfaces or other surfaces where texture may vary. Illumination cannot generally be varied and registration, alignment and detection errors may compromise the inspection process between machines and/or operators and even between exposures. Throughput of either manual or automated processes is extremely limited.

SUMMARY OF THE INVENTION

It is therefore an object of the present invention to provide an automated inspection system which allows high-speed and high throughput inspection of selected surface features on printed wiring board surfaces, particularly those surfaces of laminate chip carriers which require a high degree of uniformity and flatness for component mounting.

It is another object of the invention to provide an automated inspection system having the capability of capturing image data with differing illumination at high speed and using the separate acquisitions in combinations to detect imperfections.

It is a further object of the invention to provide control of an illumination system, particularly an illumination system using light-emitting diodes, by using a programmable current source (rather than pulse width modulation).

It is yet another object of the invention to process acquired image data without a need to align the image to any reference and to develop a self-aligned reference mask from the acquired image.

It is yet another object of the invention to provide an automated inspection system which is capable of identifying potential surface defects independently of comparison with an idealized design image.

It is a yet further object of the invention to provide an automated inspection system in which potential defects can be verified by an operator without further acquisition of data or imagery and without transfer of an inspected object to a different inspection machine to thus provide a capability of observing all defect data for an inspected piece concurrently and as soon as inspection is completed.

In order to accomplish these and other objects of the invention, an automated inspection system is provided comprising an area scan image sensor, a translation arrangement for allowing multiple inspection exposures to be made in registration with each other, digital signal processing for enhancement filtering, segmentation and binary processing of images made by the area scan image sensor, and an image presentation control arrangement for verification of defects by an operator of said automated inspection system using said automated inspection system.

In accordance with another aspect of the invention, a method of optical inspection is provided including the steps of forming a dilated aperture mask from design artwork data including rules corresponding to a surface to be inspected, capturing an inspection image, and masking the inspection image with the dilated aperture mask in order to limit the amount of image data to be processed. The invention thus develops an inspection image reference mask from the inspection image which is self-aligned thereto and the inspection image reference mask can then be compared to rules to detect defects in the mask itself, as well as being applied to defects found in the inspection image and thus limit them to critical areas of the geometry of the part.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
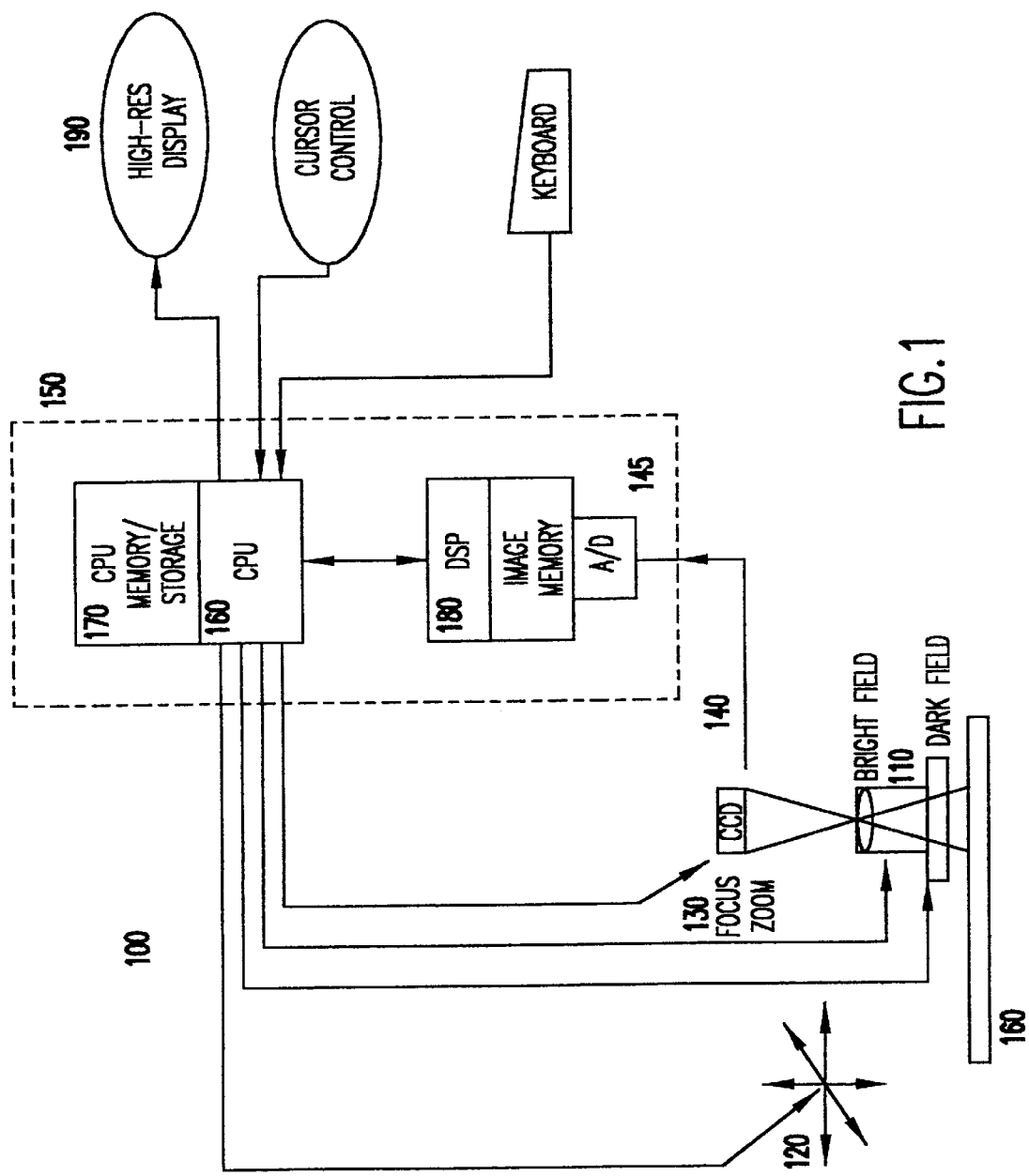
FIG. 1 is a high level block diagram of the major elements of a preferred embodiment of an automated inspection system in accordance with the invention.

Referring now to the drawings, and more particularly to FIG. 1, there is shown a high-level block diagram of a preferred form 100 of the invention. While some features of FIG. 1 may be known in automated inspection systems not directed to or adapted for surface inspection, as alluded to above, and some individual elements are commercially available so that, as is preferred, the system can have a modular architecture which is easily reconfigurable for specific inspection tasks, the combination of elements depicted is, in fact, particularly adapted thereto. Further, at the level of abstraction represented in FIG. 1, the general organization of the invention may appear more similar to known systems than may, in fact, be the case, as will become evident from the following discussion. Accordingly, no portion of FIG. 1 is admitted to be prior art in regard to the present invention.

For example, all optical inspection systems, including known systems, require an arrangement 110 for illumination of the object under inspection. However, in general, the illumination arrangement will be optimized for a given illumination pattern and direction. In contrast, in the case of the present invention, the illumination arrangement 110 provides a plurality of illumination patterns as will be discussed in more detail in regard to FIG. 2. Likewise, while known automated optical inspection systems provide for imaging of an array of areas by scanning, transfer tables and the like, the present invention provides translation and indexing in three orthogonal directions as schematically indicated at 120 and the provision of variable imaging area by zoom optics as indicated at 130. In this regard, it should also be appreciated that line scan image sensors preclude the use of a ring light form of illumination which has been found by the inventors to be particularly advantageous for imaging of surface irregularities.

Similarly, while automated inspection systems require some imaging device, line scan CCD sensors are generally employed while, in contrast, the present invention provides an area scan sensor 140. Additionally, in combination therewith, the automated control arrangement 150 of the preferred embodiment of the invention provides numerous facilities not generally provided in automated inspection systems, as will be described below.

Further, while automated inspection systems generally will include a data processor for control of the inspection process and image processing capability, the invention provides for substantial reduction of the data processed whereas more powerful or special purpose processors are generally required in known automated inspection systems. In fact, the system of the invention is preferably implemented with an off-the-shelf dedicated processor such as a vision processor board 180 comprised of a digital signal processor (DSP) and image memory that captures and processes image data (which can be accomplished with a sampling analog-to-digital converter 145). Thus no custom hardware is required, as is usually the case in known automated inspection systems. Current personal computers also generally have or can readily be provided with sufficient image memory 170 and program storage 180 for practice of the invention in regard to system control and data retention.

In this regard, control of image acquisition and digital signal processing performed by a vision processor 180 and control of illumination, camera optics, and table motion, as well as control of the vision processor by the central processing unit 160 and their associated mmemory and storage are the principal functions of the control system 150. Of these functions, the image processing function is by far the most computationally intensive but is simplified by the facility for inspection for inspecting only selected features of the product under test and by the facility for avoiding processing for registration and producing multiple, self-aligning, diversely illuminated images of areas of interest in accordance with the invention. In addition, the control system preferably allows the operator to designate such areas of interest on the surface being inspected in a simple and straightforward manner.

In accordance with the invention, images are acquired by use of a camera including an area scan CCD sensor 140 positioned parallel to the surface to be inspected. The camera/sensor is preferably provided with the Z-axis portion of translation arrangement 120 which should have sufficient travel to accommodate differences in thickness of product to be inspected. It is preferred, but not critical to the practice of the invention, to provide X-axis translation for the camera/sensor and Y-axis translation for the product. Separation of the portions of the translation arrangement 120 in this way distributes movement in such a way that one large stage, X or Y, does not have to carry the other and thus has less weight to carry. The Z stage is much smaller and thus can be carried by the X stage with no significant reduction in performance. The size of the surface to be inspected is limited only by the orthogonal translation distances provided. Translation of twenty inches in the X and Y axes is considered adequate for the practice of the invention at the present time for current and foreseeable semiconductor packages. These dimensions allow for inspection of individual printed wiring boards or strips or work panel formats of chip carriers.

Since sizes and spacings of wirebond pads and other features vary greatly among current designs, use of a motorized zoom lens 130 is preferred to accommodate requirements for different optical magnifications. Additionally, it has been found that a zoom lens is particularly useful for defect verification where greater magnification or a larger field of view is particularly convenient.

Figure 2:
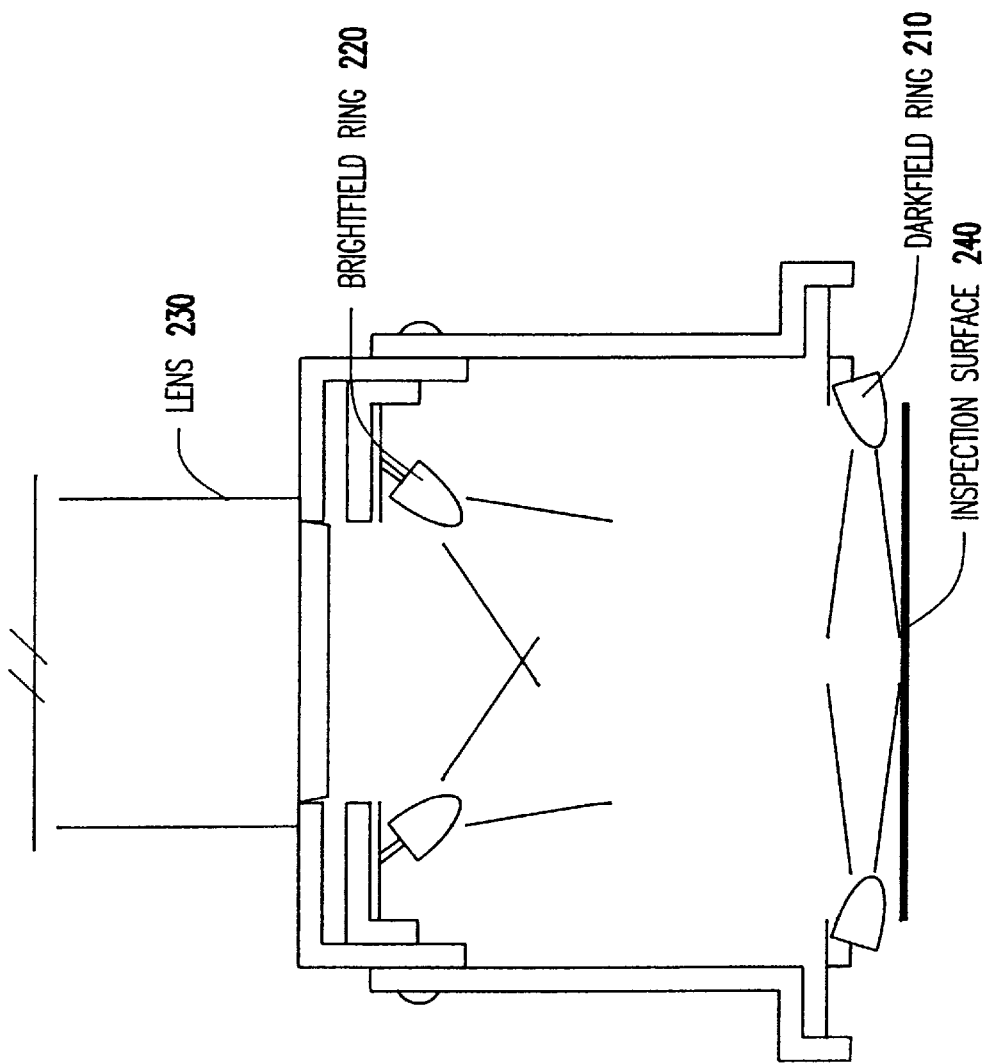
FIG. 2 is a cross-sectional and schematic view of an illumination system particularly suited to the inspection of metallic surfaces.

Referring now to FIGS. 2–5, the illumination arrangement 110 in accordance with the invention will now be described. In FIG. 2, the production of illumination fields which are substantially complementary for purposes of surface inspection are shown. Specifically, since the shape of potential defects is random and arbitrary it is desirable to avoid directional lighting which might be less effective in regard to some defect shapes and orientations than others. For this reason, a line scan arrangement which precludes ring light illumination is not well-adapted to this type of surface inspection operation. Accordingly, it is preferred to provide non-directional illumination by ring lights which provide substantially uniform illumination from all directions around the lens or observation axis.

However, to achieve illumination fields which are complementary as well as being non-directional, the angle of illumination to the surface being inspected is made as different as possible with each of a pair of ring lights. It should be understood that bright field illumination is generally considered to be sufficient for imaging of surface irregularities but the use of both dark field and bright field illumination in sequence or together provides additional data for enhancement of image processing and defect discrimination as will be described in greater detail below.

The difference in the angle of illumination of ring lights 210, 220 produces so-called dark field and bright field illumination, respectively. That is, for a metallic surface which is largely specularly reflecting in the absence of potential defects, illumination from a low angle will reflect very little light toward lens 230 from inspection surface 240. On the other hand, surface irregularities such as texture, nodules and the rims of pits will reflect more light toward lens 230 than a specularly reflecting planar surface.

In a complementary fashion, bright field illumination from a high angle produced by ring light 220 relative to the inspected surface 240 will specularly reflect substantial amounts of light toward lens 230 in the absence of surface irregularities and the amount of light so reflected will be diminished by surface irregularities and texture. Thus, the two light patterns produce reflections which are substantially complementary relative to surface textures and irregularities which darken regions of the bright field illumination pattern and are highlighted by the dark field illumination pattern. Further, large surface irregularities will generally cause relationships between the image patterns of dark field and bright field illumination which will effectively function as "signatures" for such defects and support a determination of their size and shape.

Figure 3:
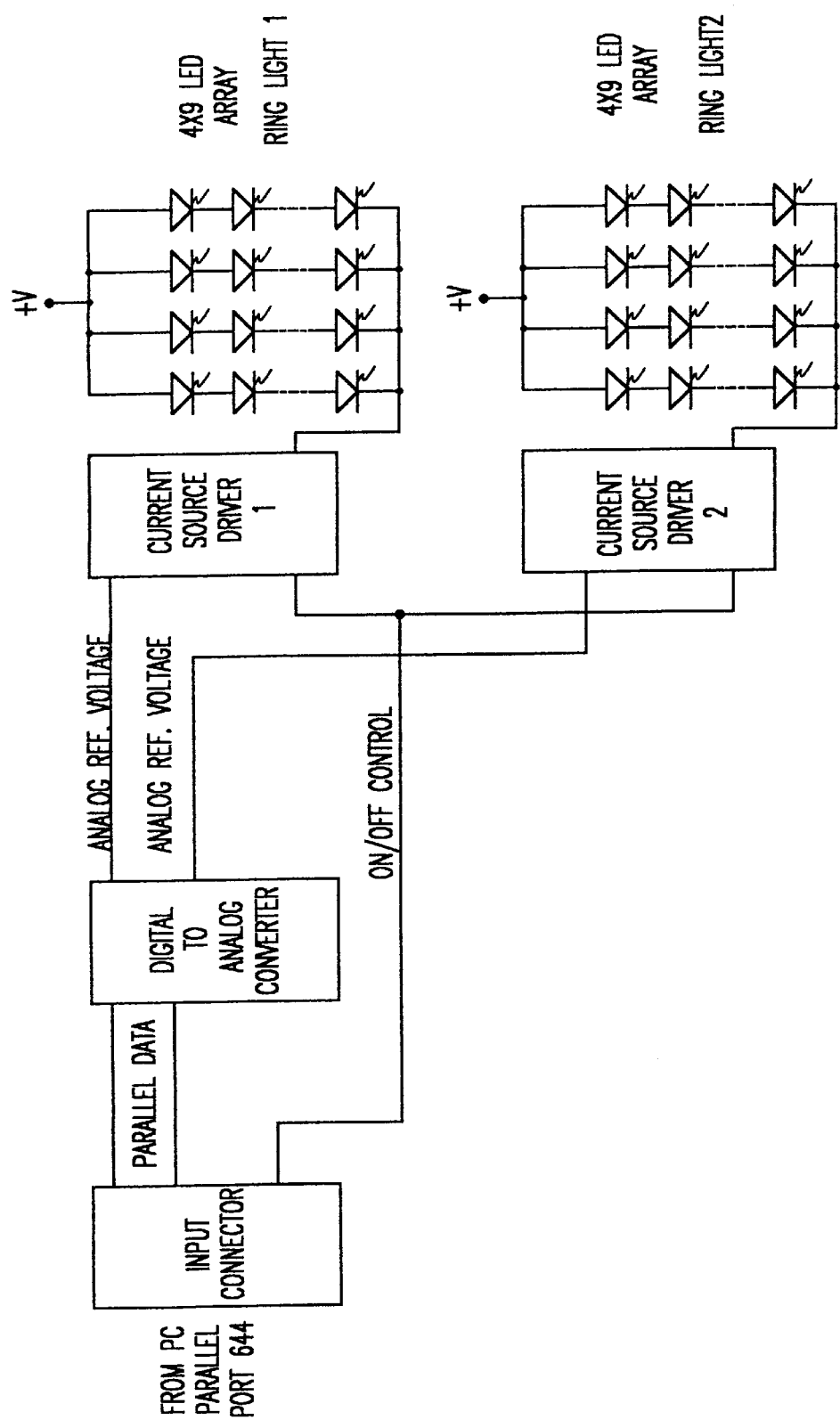
FIG. 3 illustrates the preferred connections of the LEDs of the illumination arrangements of FIGS. 4 and 5 as partially shown therein and preferred drive circuitry therefor.

FIG. 3 illustrates the preferred technique of wiring multiple groups of LEDs in series with groups connected in parallel to a programmable current source. Light output of LEDs is substantially a function of current, and series connection of LEDs in groups assists in obtaining uniformity of illumination (e.g. uniformity of LED brightness with the LEDs in a geometrically uniform array) and further by averaging manufacturing tolerances of LEDs that can have slightly different voltage drops across their respective pn junctions.

Figure 4:
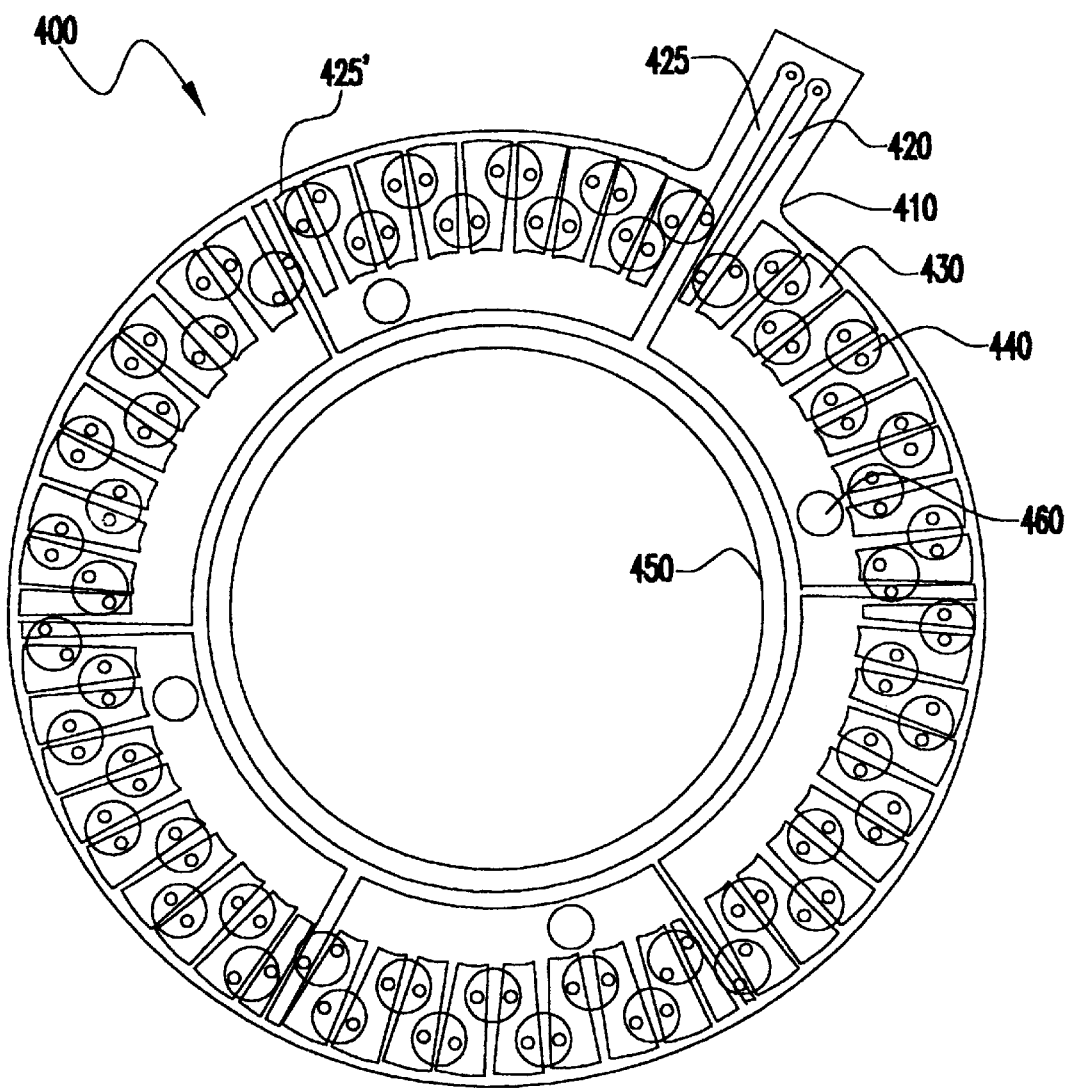
FIGS. 4 and 5 are axial views of a preferred form of light field and dark field illumination arrangements in accordance with a preferred embodiment of the invention.
Figure 4A:
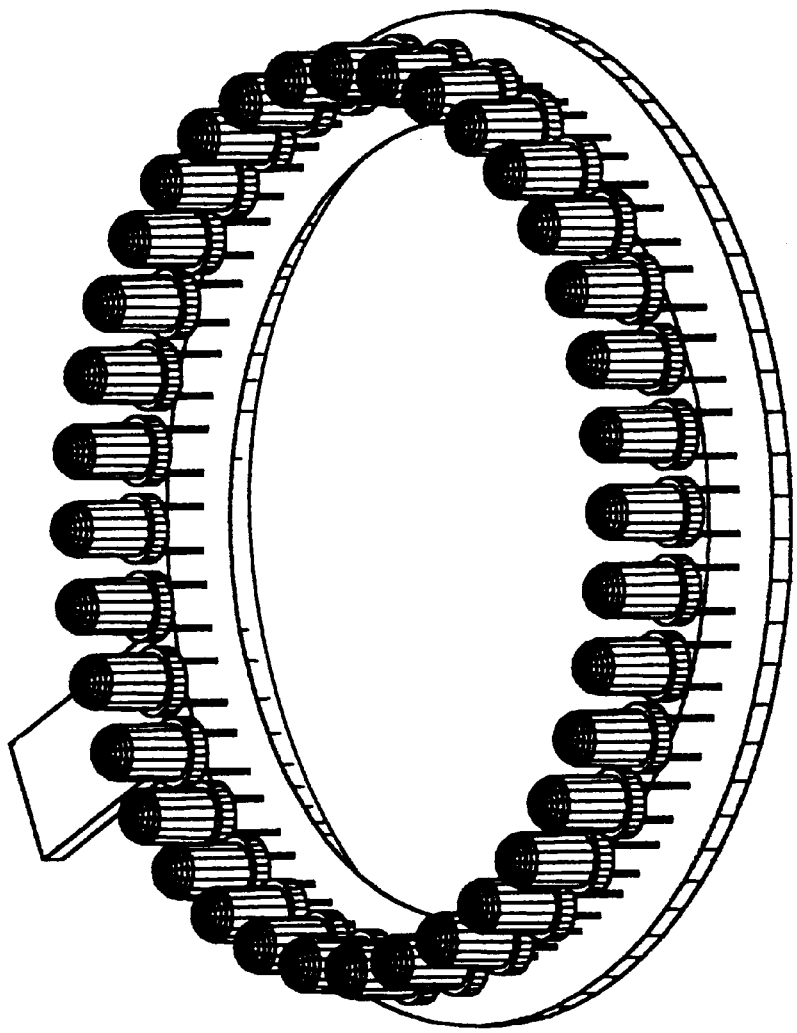
FIGS. 4A and 5A are isometric views of the illumination arrangements of FIGS. 4 and 5, respectively.
Figure 5:
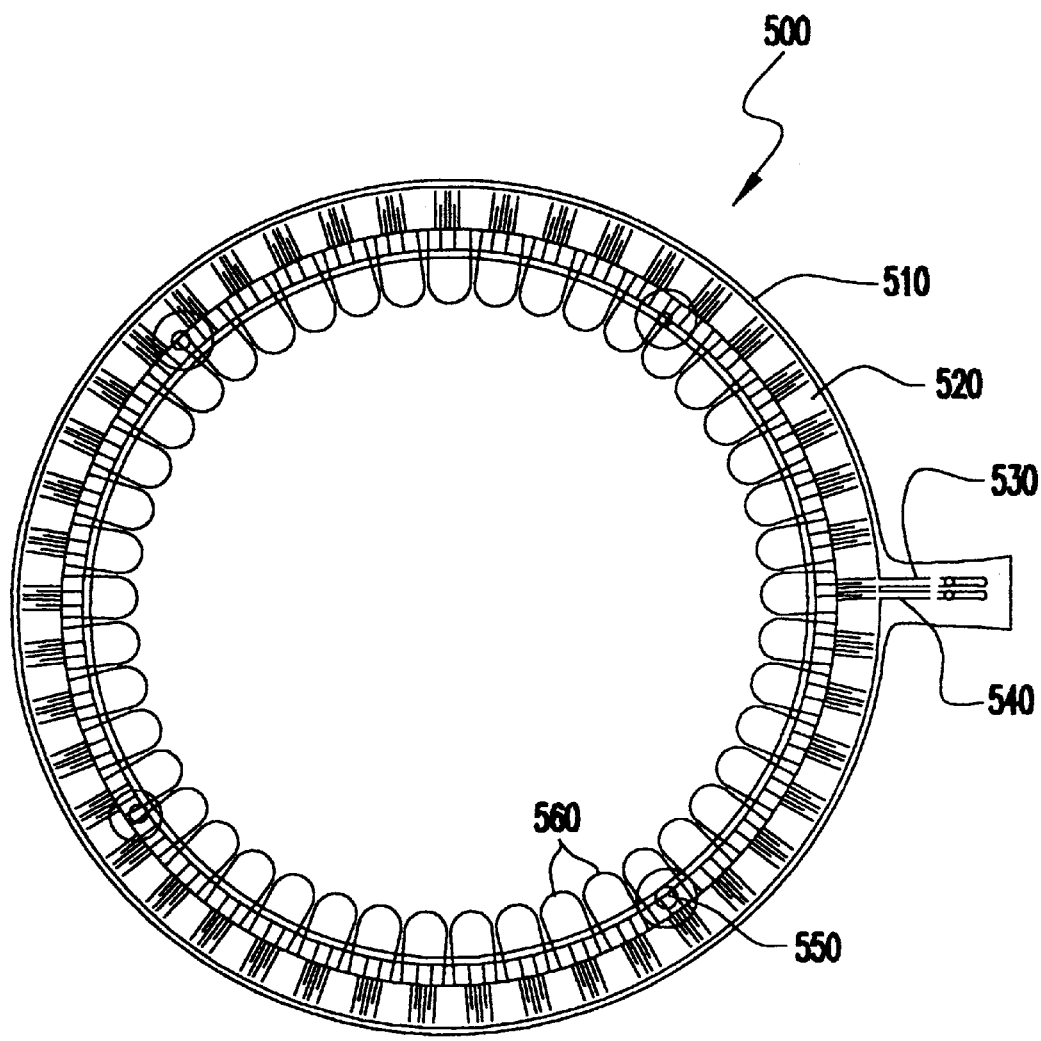
Figure 5A:
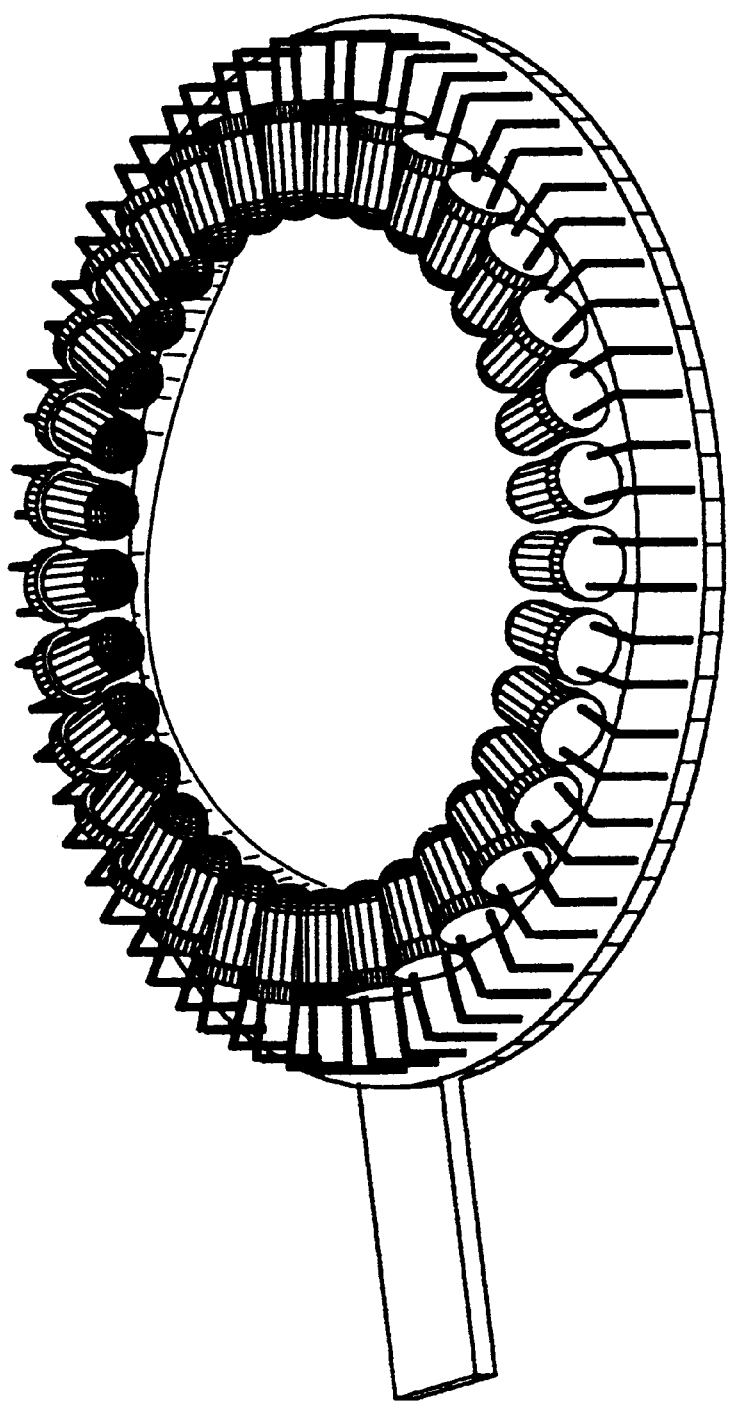
Figure 5B:
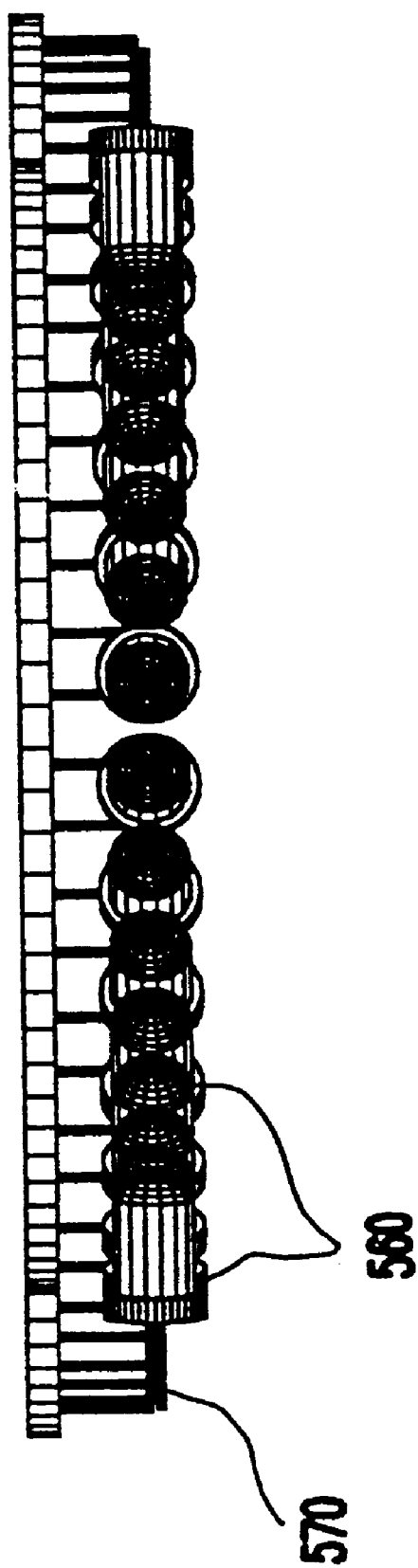
FIG. 5B is a side elevation view of the illumination arrangement of FIG. 5.

Referring now to FIGS. 4 and 5, plan views of the bright field and dark field ring lights are respectively shown. Perspective or isometric views are shown in FIGS. 4A and 5A, respectively. A side elevation view of the ring light of FIG. 5 is shown in FIG. 5B. Light emitting diodes (LEDs) are preferred as illumination sources for both since their spectral content is very stable (for a well-regulated power supply), power and heat dissipation requirements are modest, no significant degradation or aging is caused by on/off cycling and response time to the application and removal of power is very fast. Additionally, packaging of LEDs generally includes a lens arrangement which controls the solid angle of illumination adequately for practice of the invention without the use of light baffles or other illumination angle control devices. However, it should be understood that such baffles, light conducting structures such as fiber optics and the like could be used if desired or found to be advantageous for certain geometries.

The bright field ring light 400 is shown in plan view on FIG. 4. This arrangement need not comprise anything more complex than an annular circuit board 410 of sufficient rigidity to maintain a stable, preferably substantially planar form. A power electrode 420 and an annular common electrode 425 with periodic projections 425' are preferably provided. A plurality of lands 430 are also provided to facilitate a plurality of LEDs to be connected between electrodes 420 and 425 (425') in the series-parallel fashion shown in FIG. 3. It should be understood from FIGS. 4 and 5 that some jumper connections are provided on the back side of ring light 400 (and hence are obscured from view in FIGS. 4 and 5) to complete the circuit connections shown in FIG. 3. The electrical connections of the LEDs 440 to the lands 430, preferably by soldering, also provides a convenient mounting structure for the individual LEDs which is of high reliability and stability. This mounting technique is also very compact in the axial direction of the lens as is generally desirable.

The inner diameter 450 of the bright field ring light is preferably chosen to match the diameter of the lens system 230 (FIG. 2) and should generally be as small as the lens system 230 will allow in order to obtain the most nearly axial lighting direction possible but is otherwise non-critical and unimportant to the practice of the invention. Similarly, the mounting arrangement of the bright field ring light structure, depicted as four mounting holes 360 is substantially arbitrary and may be arranged with any convenient structure in any convenient manner.

Referring to FIG. 5, a preferred form of the dark field ring light 500 is shown in plan view. This arrangement is intended to provide illumination of the inspected surface at a very shallow angle to the surface rather than substantially perpendicular thereto as provided by the bright field ring light described above. To perform this function, an annular frame 510 for supporting the bodies of a plurality of LEDs and electrical connections are made thereto with a flexible circuit board 520 to which the LEDs 560 and power connections 530, 540 may be connected by solder or the like. Similarly, mounting provisions, depicted as mounting holes 550, can be of any convenient form. LEDs 560 can be installed and bent to form the ring as shown in FIG. 5B. A fixture designed to facilitate accurate forming of LED leads 570 could be used although a high degree of accuracy is not required. That is, sufficient accuracy of positioning of the LEDs for practice of the invention could be achieved without a special fixture for shaping the LED leads.

The bright field light ring 400 and the dark field light ring 500 can be thus energized individually or together and can be easily controlled in brightness by the current applied rather than by the more common pulse width modulation of energization. Current control provides the additional advantage of providing flicker-free illumination which need not be synchronized to the imaging exposure or vice-versa.

As indicated above, the images produced by the different forms of illumination and surface irregularities are largely complementary and can be made in rapid sequence at the same location using an area scan imaging device (e.g. a CCD sensor). Additionally, the alteration of image brightness with any particular parameter of surface irregularity is generally non-linear and additional information can often be acquired by imaging when the surface is simultaneously illuminated by both the bright field ring light 400 and the dark field ring light 500 at the same or different intensities. The patterns and intensities of illumination which can thus be developed for inspection imaging are readily controlled by automated control arrangement 150 (FIG. 1) which will now be discussed in detail in connection with FIGS. 6 and 7.

Figure 6:
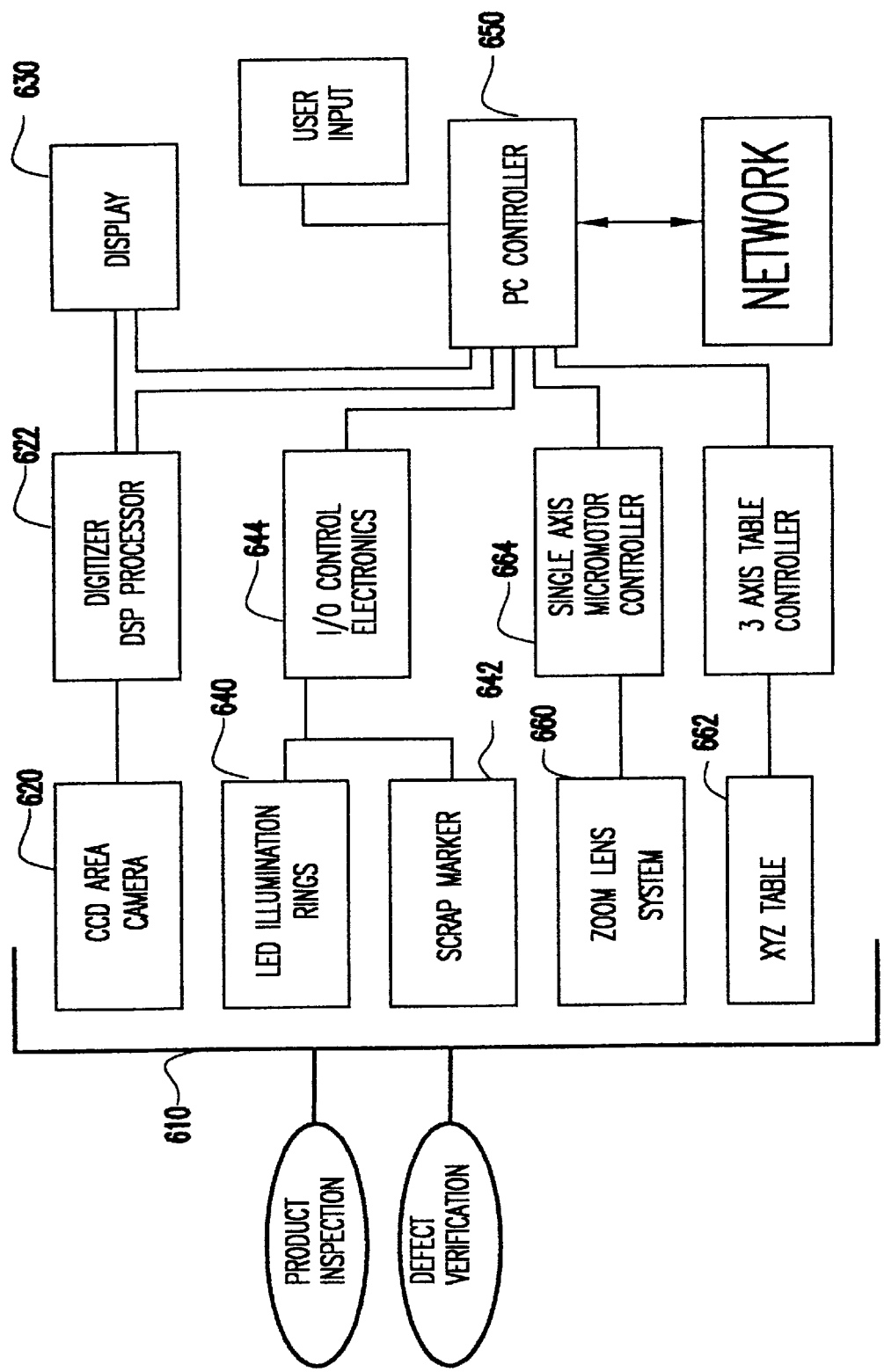
FIG. 6 is a functional block diagram of a preferred embodiment of the invention.

FIG. 6 is a functional block diagram of the system in accordance with the invention. While the block diagram of FIG. 6 is at a high level of abstraction comparable to that of FIG. 1, it is arranged to particularly illustrate the functions provided by or under control of processor 160. It should also be appreciated that substantially the same functions are performed whether the system is being utilized for product inspection or defect verification, as indicated by bracket 610.

Image data is acquired by CCD area camera 620, as discussed above, while sampling and digitizing of the acquired data is performed by digitizer 622 responsive to PC controller 650. It is preferred that digital signal processing (DSP) is also performed on the digitized data for image enhancement or the like. The results of the image data digitizing and/or signal processing can be directly viewed on display 630, also under control of PC controller 650. It should be understood that the generation of a high resolution display is also computationally intensive and real-time display of images as they are acquired and processed may not be desirable when high throughput of the inspection system is of paramount importance.

It is considered to be an important feature of the invention to make exposures in a step-and-repeat fashion while the camera is stationary relative to an area of interest. As alluded to above, a single bright field image may be sufficient to detect any existing defects, particularly when non-directional illumination is employed. As noted above, imaging of an area with a camera which is stationary relative to the surface at the time of exposure enables the use of non-directional illumination. By the same token, the invention further exploits the provision of a momentarily stationary camera by permitting a plurality of exposures to be made with the camera in the same position relative to the surface being inspected.

To provide additional information which can be advantageously used for defect discrimination, different illumination, preferably of the bright field and dark field types, or both, is used during different exposures at the same camera location. The illumination pattern, of whatever types may be preferred, is controlled by custom I/O control electronics connected to the parallel port of a PC 644 (also shown in FIG. 3), which can directly and selectively control application of power to one or more of the ring lights, as described above. Additionally, as a perfecting feature of the invention, provision can be made to mark parts to be scrapped if a defect is unequivocally discriminated.

The apparatus for performing this function is collectively indicated at 642 since various suitable arrangements are known and, in any event, the details thereof are not at all critical or even important to the practice of the invention. The PC controller 650 similarly provides signals to the three-axis "table" controller 664 for positioning the camera and lens relative to the surface to be inspected, as shown at 662, and to the single axis controller to control the field of view and/or optical magnification of zoom lens 130 (FIG. 1), as shown at 660.

Figure 7:
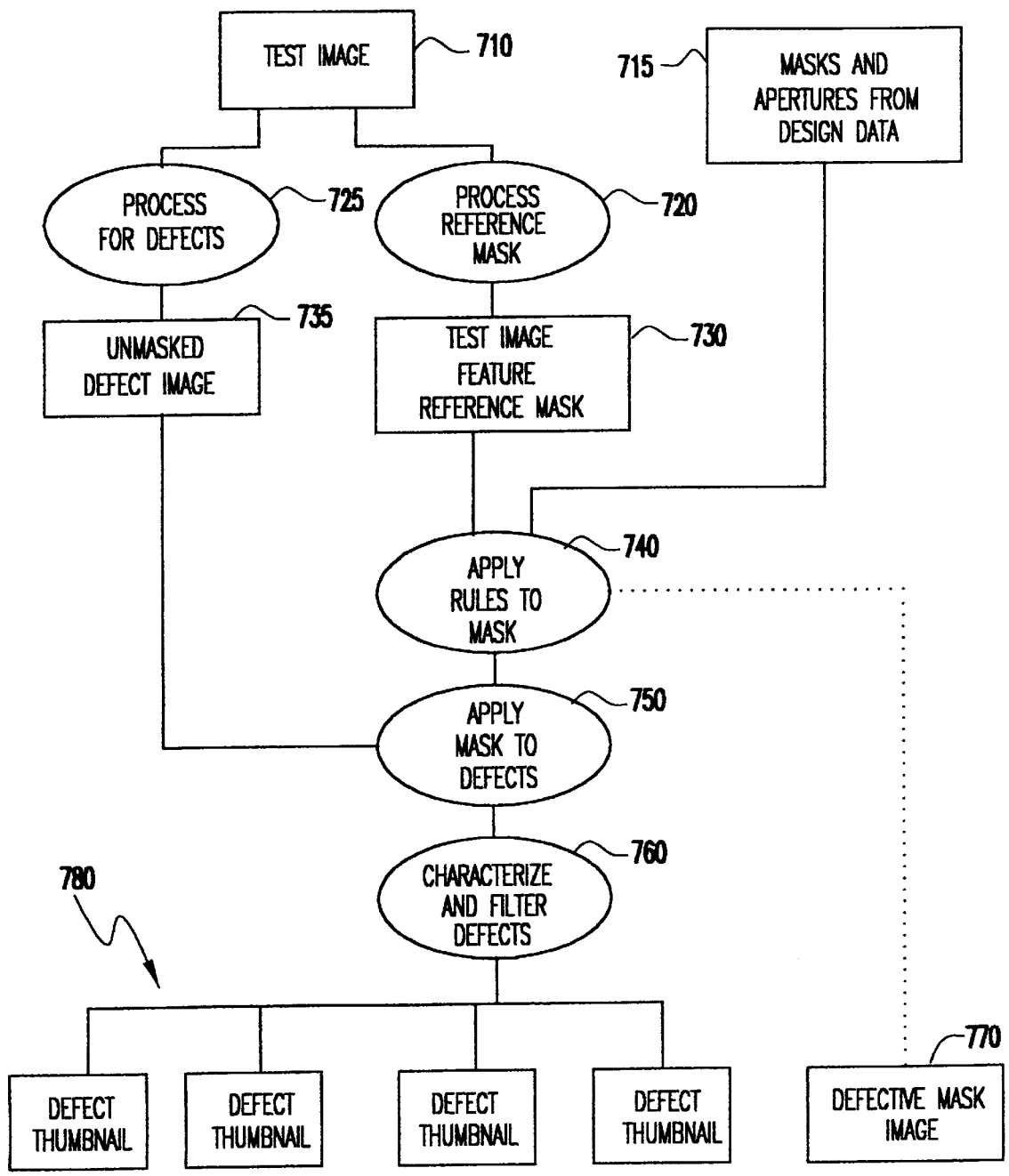
FIGS. 7 and 8 are a flow diagram of a preferred control arrangement illustrating operation of the invention and an illustration of the preferred self-registering inspection process provided by the invention, respectively.
Figure 8:
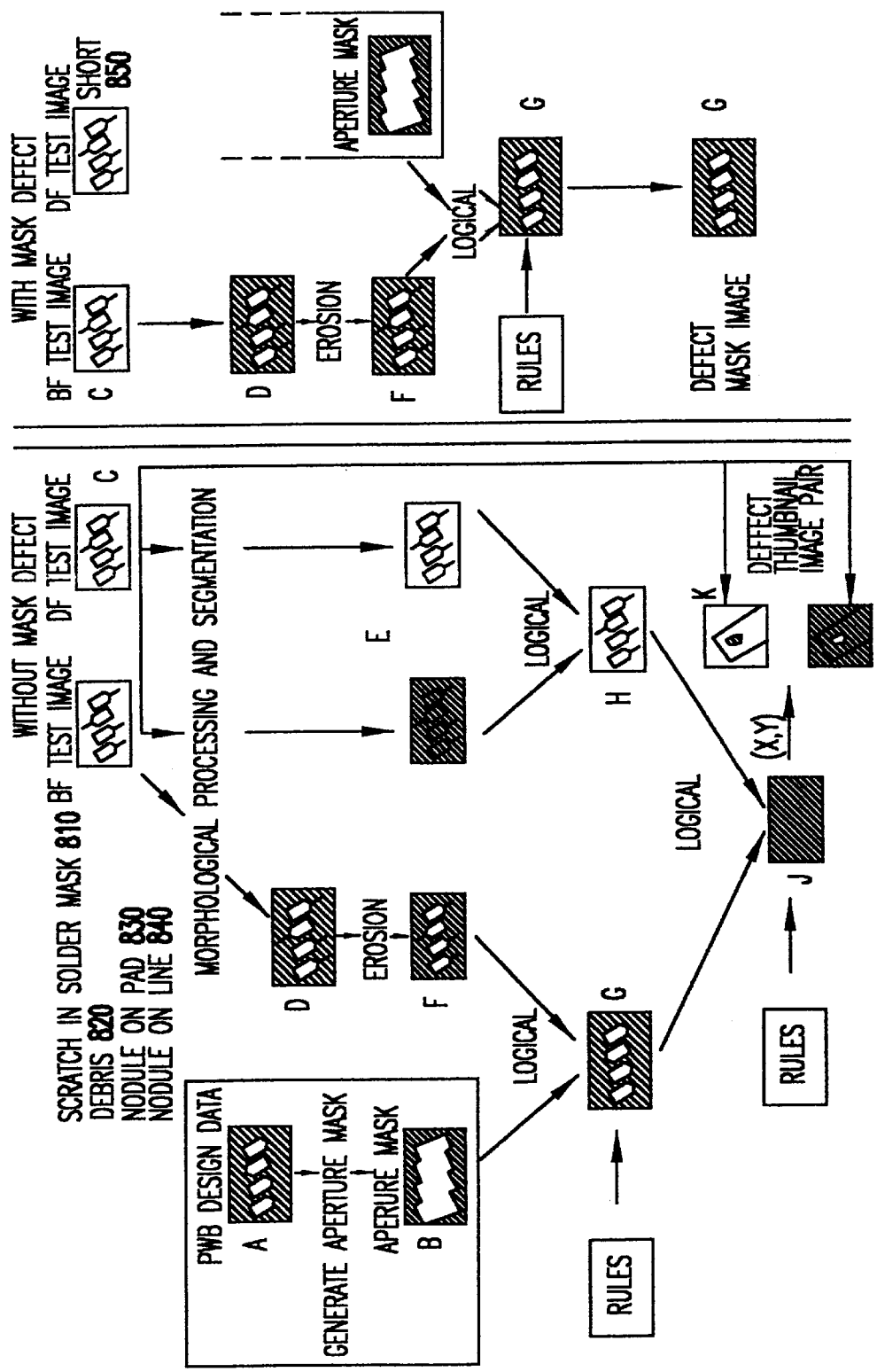

Referring now to FIGS. 7 and 8, the operation of a preferred embodiment of the invention will now be discussed. At the outset, it should be understood that it is considered preferable for an overall application to be provided which will perform the desired functions which will now be discussed. It should also be appreciated that the currently preferred image processing functions, themselves, as will be briefly summarized below, are well-understood and generally known in the art. However, any desired image processing which may be found to be effective for discrimination of surface irregularities can be employed in the practice of the invention.

It is considered preferable that the image processing and defect discrimination be integrated with the application in order to achieve some economies of processing overhead and storage but the principles of the invention can be practiced without the necessity of doing so. It is also considered to be an important feature of the invention to provide self-registration of the inspection function which significantly reduces image processing operations and greatly promotes ease of use.

The preferred application is therefore arranged to provide full tool function and a graphical user interface (GUI) which leads the operator to initialize the system and perform required calibrations in a logical order before applying the inspection process to manufactured product. The facility for operator control of the areas of interest to be inspected is also provided and serves to limit the amount of data acquired and processed.

The application preferably provides control of major functions through the use of a menu including Load, Align, Test, Calibration, Verify, Move and Edit commands. The system is first started by performing necessary calibrations including a homing operation for the positioning "table" (however configured), measuring optical magnification, and acquiring a sample of background illumination for each illumination pattern to be employed, if required. Preferably, menu choices in general are not rendered active until required procedures preliminary thereto are performed; limiting functions to those which it is possible to properly perform at any given time.

Figure 9:
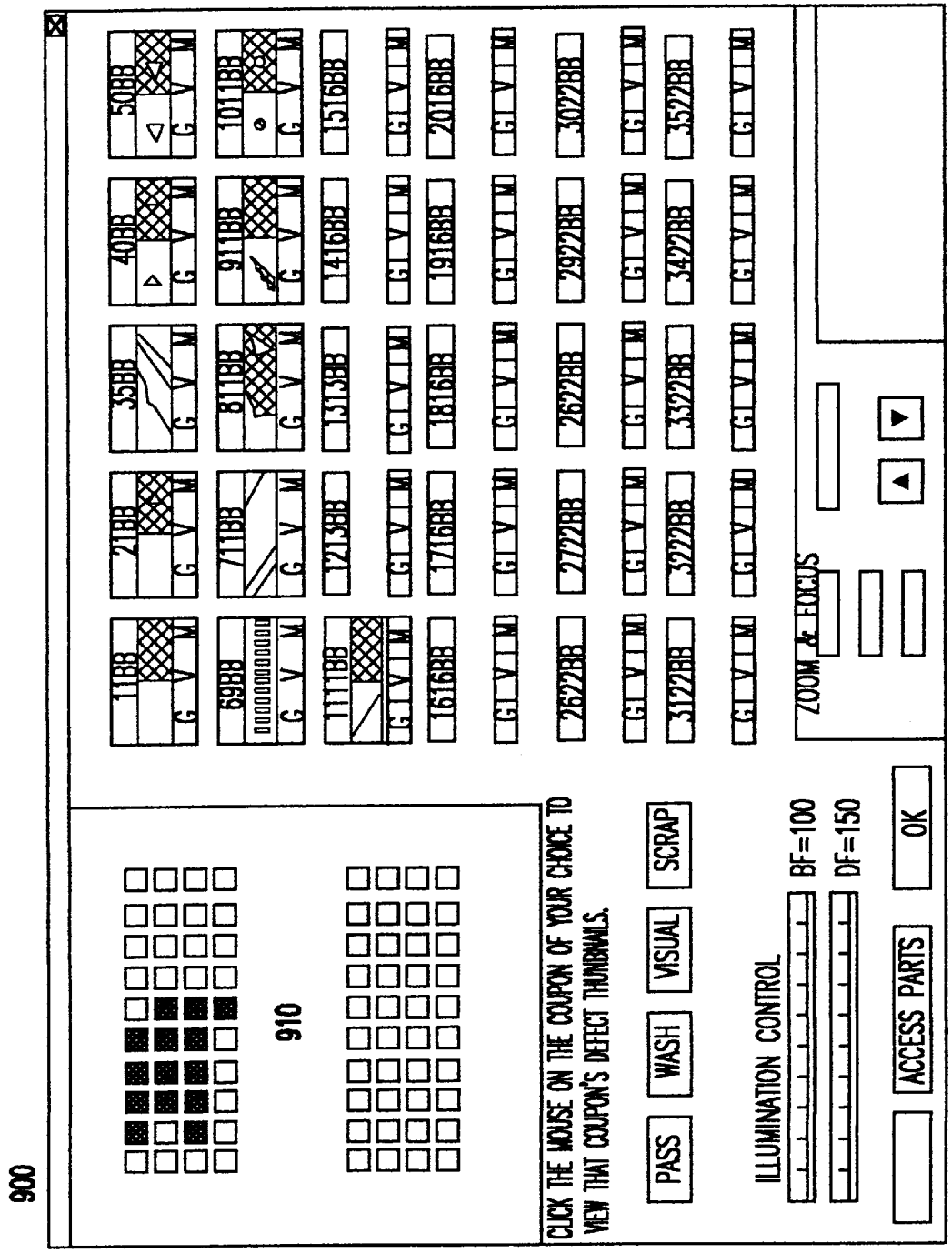
FIG. 9 is a view of an exemplary inspection screen display in accordance with the invention.

Inspection is performed by loading a data file corresponding to a product to be inspected from a list of available part numbers. A graphical image showing the parts (e.g. FIG. 9) to be inspected in their positions thereon is displayed for selection of the parts to be inspected in order to avoid inspection of "pre-scrapped" parts or pieces or locations on the chuck which may not be loaded with product. Selection is preferably done with a mouse or other pointing device in connection with the graphical user interface (GUI). Alternatively or supplementary thereto, image recognition of scrap markings could be provided to exclude particular objects or pieces (or unloaded regions of the chuck) from the inspection process.

Parts are loaded onto a vacuum chuck in a tray or other holding device and vacuum is applied to hold them in place. A pre-alignment process is performed to roughly locate each individual chip carrier product on the chuck since most handler trays allow for a large amount of variability in position of each piece within the tray relative to the size of inspected features and to the optical resolution of the system. Each piece is individually located prior to inspection by searching for one or more alignment fiducials on each piece. As long as each fiducial appears within the field of view of the camera (i.e. position error of the piece is not too great), the translational and rotational error from nominal position can be adjusted for when the piece is inspected.

Multiple display options during inspection allow for varying degrees of display of images either acquired or in various stages of processing, as well as defects found as resulting from the processing of acquired images. However, for a given level of CPU processing power, inspection will be executed more rapidly without generation of displayed images. Therefore the default option is to display nothing during inspection.

During the inspection process, any potential defects are located in the original bright field and dark field images. A small image segment, or "thumbnail" image is copied from both original images, forming a pair of thumbnails that exhibit a potential defect, and stored for later viewing during a verification process. These copies are made while inspection continues so that the potential defect location does not have to be revisited in order to see what the defect looks like, although the capability of revisiting the site and to view it at higher magnification is also provided. Capturing all potential defect images during inspection and thus elimination of a need to revisit the site allows for all potential defects for an inspected piece to be displayed at once in the verification window. Viewing all potential defects at the same time is advantageous because if any one of the potential defects is cause to scrap the part, the other defect calls do not require any extra time to review, as is the case when defect calls have to be viewed in serial fashion.

It should be noted that the defect images can be provided to another processor (e.g. over a network) for defect verification, to further increase machine time available for inspection and inspection operation throughput. While such a variation of the invention would increase the number of processors, displays and operators, advantages are still provided over known systems since the object need not be present in or transferred to the machine from which verification is done.

The Verify menu selection is considered to be an important capability of the invention since defect verification on the same machine saves substantial operator effort and processing time for registration, rotation and scaling to inspect potential defects detected on another machine, as is the current practice. The verification facility (FIG. 9) preferably includes a full-screen display window 900 that can be reviewed after the inspection process is complete for all pieces on the chuck. A graphical map 910 for the chuck in the form of a schematic indication of the locations of various pieces held thereon is displayed and color is preferably used presence (e.g. red) or absence (e.g. green) of defect calls for each inspected piece.

From this graphical map, a piece can be selected and a group of potential defect thumbnail image pairs are displayed with functional buttons adjacent each pair. The buttons can be used to either move the camera over the potential defect areas to view the surface in a live video window or view the existing thumbnails in larger windows. In the first case, zoom of the lens can be beneficially used for a magnified view of the potential defect. Once a defect is verified in this manner, a scrap marker can be placed on the defective piece to exclude the piece from further processes.

A table jog window contains utilities for viewing live images and for moving the camera to any location within the work area. In the latter case, a graphic map can be displayed and desired camera coordinates typed in, selected with a mouse and cursor image on the map or the like. Fine positioning can also be provided in a "jog" mode in which the camera can be shifted by fractional increments in coordinate directions.

The Edit menu selection provides for easy reading and/or adjustment of inspection tolerances default operations and inspection sequences and the like. System parameters are preferably loaded from a system file, viewed in a window and adjustable from within the application program. Product inspection parameters are loaded and similarly viewed and changed if the operator is authorized to do so. Each product data file contains a graphical representation of the areas to be inspected on the product and all necessary inspection parameters, such as the algorithms to be run for each feature type, maximum defect size allowed and the like.

This feature of the invention allows increased flexibility of use in automated operations since tests and inspections can be sequentially run on different products without a need for the operator to reset the inspection and test parameters for respective products. While selection of the product from a list is presently preferred in order to load the test and inspection parameters from a product file, provision of character, feature or object recognition in a manner itself well-understood in the art from a "macro view" image provided by the zoom lens or by images on a leader preceding a strip of product to load the test and inspection parameter file would provide "hands-off" testing of different products with different parameter sets. Such an arrangement would be of substantial convenience for in-line inspection where several products are being processed on the same conveyor system.

The algorithms which are presently preferred to process images are based on well-understood digital image processing techniques which are not at all critical to the practice of the invention. Each acquired image is either gray scale or color. Each image acquired is stored in RAM of the vision processor board.

Corrections are first performed on the "raw" camera image data. Pixel and background corrections are both optional but are considered useful for making the image more even across the sensor and field of view. Both of these operations are generally well-known in the art. Image enhancement is performed when necessary to increase image contrast. Image enhancement is preferably performed by a morphological contrast operation on the (corrected) gray-scale image.

Potential defects can be separated from an otherwise locally homogeneous area by the use of a "Tophat" filter. The particular Tophat filter preferred for a bright field image is for isolation of dark objects, which comprises a number of closings (e.g. dilation followed by erosion) of the input image minus the original input image after the closing operations. One or more such closings can be performed for both images involved in the subtraction. Conversely, a dark field image where defects would be bright areas in the image would use a Tophat filter where openings (e.g. erosion followed by a dilation) are used instead of a closing. This latter process would isolate the bright areas from a dark background. Finally, in either case, the final step is to convert the contrast enhanced image to a binary image in accordance with another threshold so that each pixel in the resultant image has a value of "0" or "1".

Having described the functions of the preferred application and the preferred image processing included in the invention, the self-registration function of the invention will now be described. This function is considered to be a particularly important and novel feature of the invention since it develops reference coordinates from the inspection image itself.

That is, since each acquired image will contain regions of interest and regions which are of no interest, the result of the Tophat filtering must be spatially filtered in some way since light and dark regions representing normal patterning of the product but other than the wirebond pads and other surfaces to be inspected will invariably be present. The approach previously used was to use the x,y coordinates of polygons to define the perimeters of regions of interest. For this to be performed reliably, alignment of the camera to the product is critical an some form of registration and rotation process to the design image of the product would generally be required.

An alternative approach in accordance with the invention is to use the inspection image, itself, by creating a mask from the input images to filter the defects. The mask is created by performing morphological operations a low-level threshold on the input image and thus can automatically locate each region of interest without critical alignment as long as the alignment is adequate to include all regions of interest within the image borders, as is assured by the pre-alignment process.

The technique actually preferred is a combination of the two techniques which will now be described with reference to FIGS. 7 and 8. Prior to inspection, a product inspection file is created from the design data file of the product (image A of FIG. 7). An aperture mask (image B) is developed by geometrical transformation and dilated to allow for some misalignment to the actual inspection image and thus defines the feature areas that are to be inspected. Design data is "unlayered" and only the features to be inspected are included in image A and dilated to form the aperture mask of image B. These operations are collectively illustrated at 715 of FIG. 7. A relatively rapidly executable pre-alignment process, as described above, can then be used to place features of the inspection image as close as possible (e.g. within the dilation dimensions) to their expected locations within the image. Then a windowing function is performed in accordance with image B on the inspection image (image C). The purpose of this windowing function is to further limit the processing required as the windowed area represents areas of interest where further processing will occur, excluding all other areas and thus speeding the process.

During inspection, inspection images C, acquired at 710 of FIG. 7, are used to create mask D (at 720 of FIG. 7) while finding certain defects in accordance with the tophat filtering through morphological operations described above. Defect image layers are created for each acquired image (image E) containing these potential defects 810, 820, 830 and 840. Mask D is further eroded to create mask F in order to reduce the size of each feature, thus eliminating feature edge effects that are evident in image layers E. These defect layers are combined by a logical operation (e.g. logical OR) as shown in combined defect layer image H, including what is present in either of the layers thereby making best use of the complementary nature of bright field and dark field illuminations by building all imaged portions of a particular defect from individual imaged portions of each exposure, as exemplified in the growth in size of defect 830.

Reference mask G is created by combining (e.g. logical AND) what is common between aperture B and mask F. This has the effect, in the example shown, of trimming line traces from the bond fingers since surface defects will not constitute a scrap condition if they are found on a non-critical area such as a line trace. Aperture B can thus limit inspection to prescribed critical areas for the given image that has some alignment error. Rules are applied to mask G to assure that the mask is correct and contains no defect condition.

Provided there is nothing defective with mask G, the final step image J is created by combining what is common between mask G and defect image layer H, which are automatically precisely aligned, to remove all unwanted feature edge effects and non-critical defects. In the example shown, the nodule on the line trace, defect 840, and the superficial scratch on the solder mask, 810, are both excluded by the application of mask G. Defect 820, the debris above the bond finger, is also excluded even though it may have been included if only mask B had been applied (with dilation to account for positioning error) to defect image layer H. Thus the only critical defect is obtained from this image and corresponds to the same exact location in the original test image, where a thumbnail image pair, K, is copied from each exposure for verification.

It should be noted that defect 850 in the form of an electrical short between fingers on the pattern will not necessarily be found by morphological processes. The operations are collwectively illustrated at 725 of FIG. 7 and also in FIG. 8 under the heading "With Mask Defect". The inspection image mask (image G) is created the same way as in the previous example and evaluated agains rules provided. In this case, the rules are violated (e.g. the number of objects found is incorrect due to the short), and the entire mask is stored as a defect for later review.

It should be appreciated from the foregoing discussion of defect detection that either bright field or dark field illumination or a mixture of the two could be used concurrently or in sequence. It is particularly useful to use both the bright and dark field images for mask creation because of their complementary nature. The contrast enhancement processes discussed above are generally complementary as are the image values in images derived therefrom. Mixtures of light may require adjustments of thresholds in the contrast enhancement process in order to suitably discriminate defects and the actual size thereof.

In view of the foregoing, it is seen that the invention provides an automated inspection system particularly adapted to the discrimination of surface defects, especially specularly reflecting materials. Exemplary surface defects include pits, mouse bites, nodules, excessively rough surfaces, chemical contamination, foreign material, stains, shorts, voids, gold voids, and missing feature areas. In practice, the efficiency of the invention to find defects closely approaches 100% as compared to about 70% efficiency of a single visual inspection and which requires multiple full visual inspections at comparable efficiency to discover substantially all defects (which the invention provides in a single operation). The area scan image sensor allows plural images with different and preferably complementary illumination at the same location and in accurate registry. Pre-alignment of the piece to be inspected is made non-critical and reduces processing time by development of a mask including areas of interest from the inspection image in connection from the design data file for the product. High-speed, high throughput inspection is provided at greater efficiency levels of operators by limitation of data and provision for both inspection and defect verification to be done in rapid sequence on a single inspection system from stored or live images. Image processing is preferably integrated with functions provided and controlled through a graphic user interface.

While the invention has been described in terms of a single preferred embodiment, those skilled in the art will recognize that the invention can be practiced with modification within the spirit and scope of the appended claims.

What is claimed is:

1. An automated inspection system, comprising:
   an area scan image sensor,
   an illumination unit which shines at least one of bright-field light and dark-field light onto a surface of a workpiece to be inspected;
   an image acquisition unit which acquires multiple inspection exposures of said area of interest while said area scan image sensor is in a stationary position relative to said surface of a workpiece to be inspected;
   a processor for performing enhancement, filtering, segmentation and binary processing of images derived from said multiple inspection exposures to locate at least one defect on said workpiece, and
   a graphical user interface which displays segmented portions of at least one of said multiple inspection exposures and said images, said interface including control means for verification of defects by an operator based on said segmented portions.

2. A system as recited in claim 1, wherein said processor locates said defect by separately processing a bright-field image and a dark-field image of said area of interest derived from said multiple inspection exposures.

3. A system as recited in claim 1, wherein said graphical user interface simultaneously displays images of multiple defects detected by said processor on said workpiece.

4. A system as recited in claim 1, wherein said processor locates said defect by generating a first mask isolating a region in one of said images where a potential defect is likely, generating a second mask from a workpiece data file that corresponds to said region without a defect, and comparing said first mask to said second mask to confirm existence of said defect.

5. A system as recited in claim 1, wherein said processor includes means for discriminating whether said defect is a critical defect or a non-critical defect.

6. A system as recited in claim 2, wherein said illumination source comprises an array of light emitting diodes.

7. A system as recited in claim 1, further including a zoom lens for imaging said surface of said workpiece onto said area scan image sensor.

8. A system as recited in claim 1, wherein said area scan image sensor is a charge coupled device sensor.

9. A method of optical inspection including the steps of
   forming a dilated aperture mask from inspection data including rules corresponding to a surface to be inspected,
   capturing an inspection image, and
   logically combining the inspection image with dilated apertures of said dilated aperture mask.

10. A method as recited in claim 9, including the further steps of
    forming an image mask from said inspection image, and
    windowing said image mask with said dilated apertures to form an inspection image reference mask.

11. A method as recited in claim 10, including the further step of
    discriminating a defect in accordance with said windowing step and said rules.

12. A method as recited in claim 9, including the further step of
    creating a defect image layer by morphological operations on said inspection image.

13. A method as recited in claim 12, wherein said morphological operations include tophat filtering.

14. A method as recited in claim 10, wherein said windowing step includes the step of
    forming an inspection image reference mask.

15. A method as recited in claim 14, including the further step of
    performing a logical operation on said image inspection reference mask and said defect image layer.

16. A method as recited in claim 15, including the further step of storing an image portion of a result of said logical operation.

17. A method as recited in claim 16, including the further steps of
    recalling and displaying said image portion, and
    verifying a defect from said displayed image.

18. A method as recited in claim 16, including the further step of
    displaying all said image portions for a given part concurrently for concurrent review and inspection.

19. A method as recited in claim 14, including the further step of
    combining defect image layers of separate exposures in a complementary fashion whereby all imaged portions of a defect are obtained.

20. A system as recited in claim 1, wherein said processor includes a filter for distinguishing said defect from locally homogeneous areas on said workpiece.

* * * * *